US011337684B2

(12) United States Patent
Zhang et al.

(10) Patent No.: US 11,337,684 B2
(45) Date of Patent: May 24, 2022

(54) OCCLUDER AND METHOD FOR SEWING OCCLUDER

(71) Applicant: Lifetech Scientific (Shenzhen) Co., Ltd., Shenzhen (CN)

(72) Inventors: Jie Zhang, Shenzhen (CN); Xianmiao Chen, Shenzhen (CN); Yueying Deng, Shenzhen (CN); Wenfeng Li, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 106 days.

(21) Appl. No.: 16/474,711

(22) PCT Filed: Dec. 19, 2017

(86) PCT No.: PCT/CN2017/117195
§ 371 (c)(1),
(2) Date: Jun. 28, 2019

(87) PCT Pub. No.: WO2018/121348
PCT Pub. Date: Jul. 5, 2018

(65) Prior Publication Data
US 2020/0383666 A1  Dec. 10, 2020

(30) Foreign Application Priority Data

Dec. 31, 2016 (CN) .......................... 201611267419.9

(51) Int. Cl.
*A61B 17/06* (2006.01)
*A61B 17/00* (2006.01)
*A61L 17/12* (2006.01)

(52) U.S. Cl.
CPC .... *A61B 17/0057* (2013.01); *A61B 17/06166* (2013.01); *A61L 17/12* (2013.01);
(Continued)

(58) Field of Classification Search
CPC .......... A61B 17/0057; A61B 17/06166; A61B 2017/00526; A61B 2017/00575;
(Continued)

(56) References Cited

U.S. PATENT DOCUMENTS 4,917,089 A * 4/1990 Sideris ............... A61B 17/0057
128/899
5,061,274 A * 10/1991 Kensey ............... A61B 17/0057
606/213
(Continued)

FOREIGN PATENT DOCUMENTS

CN      201082203 Y    7/2008
CN      101283935 A    10/2008
(Continued)

OTHER PUBLICATIONS

International Search Report dated Mar. 15, 2018 for corresponding PCT Application No. PCT/CN2017/117195.
(Continued)

*Primary Examiner* — Vi X Nguyen
(74) *Attorney, Agent, or Firm* — Raymond Sun

(57) ABSTRACT

An occluder has a first disk-shaped structure with a grid, wherein the first disk-shaped structure is woven from at least two groups of braided wires, and the two groups of braided wires are crossed to form multiple rings of crossing points. A blocking membrane is also arranged in the disk-shaped structure, with an edge of the blocking membrane connected to the outermost ring of crossing points of the multiple rings of crossing points through a sewing wire, and the number of crossing points in the outermost ring of crossing points sewn with the blocking membrane is smaller than the number of all the crossing points in the outermost ring of the crossing points. The occluder can reduce the possibility of the phenomenon where the edge of the blocking membrane cannot
(Continued)

abut against a disk face edge of the occluder, thereby improving the occlusion effect of the occluder.

7 Claims, 2 Drawing Sheets

(52) U.S. Cl.
CPC .............. *A61B 2017/00526* (2013.01); *A61B 2017/00575* (2013.01); *A61B 2017/00597* (2013.01); *A61B 2017/00601* (2013.01); *A61B 2017/00654* (2013.01); *A61B 2017/00663* (2013.01); *A61B 2017/00867* (2013.01)

(58) Field of Classification Search
CPC .......... A61B 2017/00597; A61B 2017/00601; A61B 2017/00654; A61B 2017/00663; A61B 2017/00867; A61B 2017/00592; A61B 2017/00243; A61B 2017/00606; A61B 2017/00623; A61B 17/00; A61B 17/06; A61B 17/12; A61B 17/12022; A61B 17/12145; A61B 2017/1205; A61L 17/12
See application file for complete search history.

(56) References Cited

U.S. PATENT DOCUMENTS

| | | | |
|---|---|---|---|
| 2004/0220610 A1* | 11/2004 | Kreidler | ............... B32B 27/322 606/200 |
| 2006/0224183 A1 | 10/2006 | Freudenthal | |
| 2016/0168770 A1 | 6/2016 | Heipl | |
| 2019/0076136 A1* | 3/2019 | Zhang | ............... A61B 17/12172 |
| 2019/0274668 A1* | 9/2019 | Glimsdale | .......... A61B 17/0057 |

FOREIGN PATENT DOCUMENTS

| | | |
|---|---|---|
| CN | 101933850 A | 1/2011 |
| CN | 101933850 A | 1/2011 |
| CN | 201814682 U | 5/2011 |
| CN | 206934127 U | 1/2018 |
| CN | 108261214 B | 6/2020 |
| EP | 2 606 829 | 6/2013 |
| EP | 2606829 A1 | 6/2013 |
| WO | WO2009/137755 | 11/2009 |
| WO | WO 2016/038115 A1 | 3/2016 |
| WO | WO2016/087061 | 6/2016 |

OTHER PUBLICATIONS

European Search Report dated Jul. 19, 2020 for corresponding EP Application No. EP 17 88 6551.
Office Action dated Mar. 18, 2019 for corresponding China Application No. 201611267419.9.
Office Action dated Nov. 28, 2019 for corresponding China Application No. 201611267419.9.
Office Action dated Sep. 7, 2021 for corresponding India Application No. 201917029103.

* cited by examiner

OCCLUDER AND METHOD FOR SEWING OCCLUDER

FIELD

The present disclosure relates to the technical field of medical devices, and more particularly relates to an occluder and a method for suturing an occluder.

BACKGROUND

A heart defect occluder is an implanted medical device for treating congenital heart defects, and its general structure mainly includes a sealing disk, a blocking membrane, a suture and the like. The blocking membrane has functions of occluding a defect and preventing blood shunting, and the blocking membrane is fixedly sutured on the edge of the largest diameter of the sealing disk.

At present, occluders for clinical use on the market are mostly woven by nickel-titanium alloy wires. The growth of an immature heart of a patient would be affected by a rejection of organisms, due to the long-term existence of the nickel-titanium alloy wires in a human body, and allergies and corresponding complications, and even a certain degree of damage, caused by a presence of nickel ions. In recent years, an absorbable occluder woven by a biologically degradable material (such as a macromolecular material) has been introduced. The absorbable occluder may be degraded into small molecules harmless to the human body after completing its function of blocking the heart and then excreted by the metabolism of the human body, so as to avoid any long-time influence of foreign matters in the human body.

However, because an edge of an opening of a sheath tube has a pushing effect on the suture when the sealing disk is collected into the sheath tube, stitched intersections between the suture and the grids of the sealing disk would move towards a distal end of the occluder, so that an edge of the blocking membrane would roll up. In addition, because intersections between grids of the sealing disk would move towards the distal end of the occluder when the sealing disk enters the sheath tube, and the resilience of a sealing disk woven by the macromolecular material is lower than that of a sealing disk formed by a nickel-titanium wire, the disk surface of the sealing disk of the occluder will be enlarged when the sealing disk has no external force, which will cause the edge of the blocking membrane to fail in abutting against the edge of the disk surface of the sealing disk of the occluder after the occluder is released (that is, the occluder is in a natural state that has no external force). As a result, residual shunting blood may flow in the defect part of the patient, and the defect part may not be completely occluded, so the safety and effectiveness of the operation are reduced.

SUMMARY

In view of the above, it is necessary to provide an occluder that is capable of reducing the possibility of the phenomenon that the edge of a blocking membrane may not abut against the edge of the disk surface of the occluder in a natural state. To solve the above-mentioned problems, the present disclosure adopts the following technical solution.

The present disclosure provides an occluder, including a first disk-shaped structure having grids. The first disk-shaped structure is woven by at least two groups of weaving wires. The at least two groups of weaving wires are crossed to form multiple circles of crossing points. A blocking membrane is further arranged in the first disk-shaped structure. The edge of the blocking membrane is connected with the outermost circle of crossing points of the multiple circles of crossing points through a suture, and the number of the crossing points sutured with the blocking membrane in the outermost circle of crossing points is less than that of all the crossing points in the outermost circle of crossing points. The position of the blocking membrane that is close to the edge of the blocking membrane is connected with one circle of crossing points that are located within the outermost circle of crossing points, in the multiple circles of crossing points, through the suture.

In one embodiment, a first circle of sutural pores and a second circle of sutural pores are defined in the blocking membrane. The first circle of sutural pores are farther from the center of the blocking membrane than the second circle of sutural pores, and the number of the sutural pores in the first circle of sutural pores is less than that of all the crossing points in the outermost circle of crossing points.

In one embodiment, the second circle of sutural pores are sutured to the circle of crossing points, closest to the outermost circle of crossing points, in the multiple circles of crossing points through the suture.

In one embodiment, the first circle of sutural pores are arranged at the edge of the blocking membrane.

In one embodiment, at least one sutural pore among one second circle of sutural pores is located between every two sutural pores in the first circle of sutural pores.

In one embodiment, the occluder further includes a second disk-shaped structure connected with the first disk-shaped structure and a waist part connected between the first disk-shaped structure and the second disk-shaped structure.

In one embodiment, the distal end of the first disk-shaped structure is provided with a distal sealing head, and the first ends of the at least two groups of weaving wires are collected at the distal sealing head. The proximal end of the second disk-shaped structure is provided with a proximal sealing head, and the second ends, opposite to the first ends, of the at least two groups of weaving wires are collected at the proximal sealing head.

In one embodiment, the suture includes a polylactic acid suture, and the blocking membrane includes a polylactic acid blocking membrane.

In one embodiment, the occluder is a macromolecular material occluder.

In one embodiment, the occluder is woven by 36, 72 or 144 weaving wires.

The present disclosure further provides a method for suturing an occluder. The suturing method includes: suturing the edge of a blocking membrane to the outermost circle of crossing points of multiple circles of crossing points of the occluder through a suture, and suturing the position that is close to the edge of the blocking membrane to one circle of crossing points that are located within the outermost circle of crossing points, in the multiple circles of crossing points, through the suture.

In one embodiment, the position close to the edge of the blocking membrane is sutured to the circle of crossing points closest to the outermost circle of crossing points in the multiple circles of crossing points through the suture.

In one embodiment, after the suturing has been completed, two ends of the suture are knotted.

Compared with the prior art, the occluder of the present disclosure has the advantages that after the occluder has been released from a sheath tube, one circle of crossing points, sutured with the blocking membrane and located within the outermost circle of crossing points, would move towards the outermost circle of crossing points to push the edge of the blocking membrane to move, thereby increasing the possibility that the edge of the blocking membrane abuts against the edge of the disk surface of the disk-shaped structure of the occluder; in other words, reducing the possibility that the edge of the blocking membrane may not abut against the edge of the disk surface of the occluder, increasing the possibility of completely occluding a defect part of the patient, and improving the safety and effectiveness of the operation.

DETAILED DESCRIPTION

Figure 1:
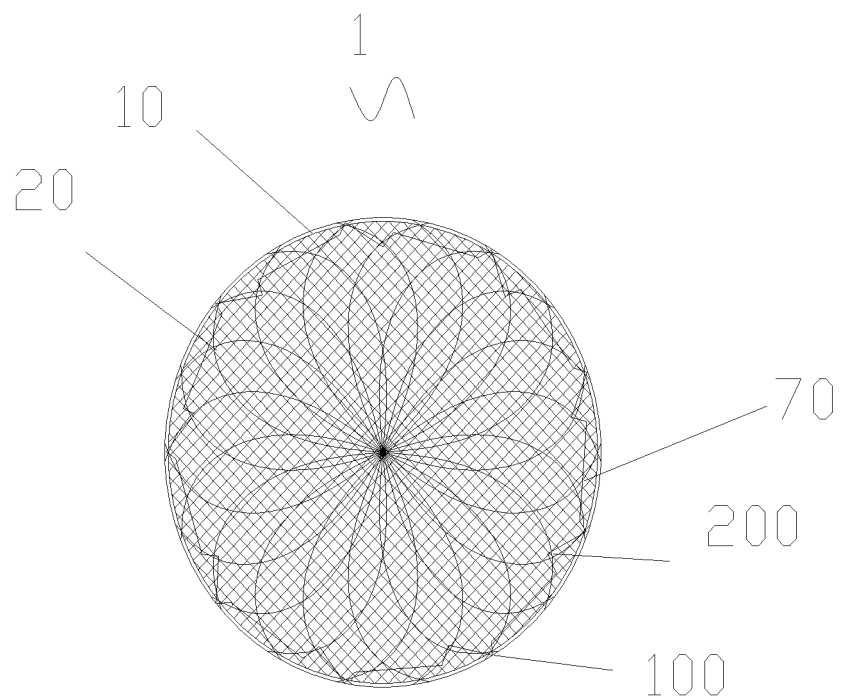
FIG. 1 is a structural schematic diagram of an occluder provided by one embodiment of the present disclosure.

To understand the objectives, technical solutions and advantages of the present disclosure clearer, the present disclosure is further described below in detail in combination with accompanying drawings and embodiments. It should be understood that specific embodiments described herein are only used to explain the present disclosure, but not intended to limit the present disclosure.

Unless otherwise defined, all technical and scientific terms used herein are the same as meanings of general understandings of those skilled in the art of the present disclosure. The terms used in the description of the present disclosure in the text are only to describe specific embodiments, not intended to limit the present disclosure. The terms "and/or" used herein include any and all combinations of one or more relevant listed items.

The inventive spirit of the present disclosure is that sutured points between a blocking membrane and an occluder are set on different sections of the occluder. After the occluder is released from a sheath tube, one circle of crossing points located within the outermost circle of crossing points and sutured with the blocking membrane would move towards the outermost circle of crossing points and push the edge of the blocking membrane to move. As a result, it is possible to increase the possibility that the edge of the blocking membrane abuts against the edge of the disk surface of a disk-shaped structure of the occluder. In other words, it is possible to reduce the possibility that the edge of the blocking membrane may not abut against the edge of the disk surface of the occluder, and it is possible to increase the possibility of completely occluding a defect part of the patient and improve the safety and effectiveness of the operation. In addition, when the occluder is collected into a bundle and pulled into the sheath tube, the sutured points between the blocking membrane and the disk-shaped structure are located on different sections, so that the diameter of the section of the occluder may be decreased, and the resistance and the pushing action of the opening of the sheath tube on the suture and the blocking membrane are reduced, when the occluder is put into the sheath tube. In addition, the number of sutured points on the same section is decreased, so that the number of acting points of the opening of the sheath tube on the suture is greatly decreased, thereby reducing the possibility that the opening of the sheath tube pushes the sutured points, which can cause crossing points sutured on the disk-shaped structure of the occluder by the suture to move towards the distal end of the occluder when the occluder is put into the sheath tube. Finally, the possibility of rolling up of the edge of the blocking membrane may be effectively reduced. In this manner, the risk of disconnection between the blocking membrane and the crossing pints when the occluder is put into the sheath tube may be lowered, and the possibility that the occluder in a natural state completely occludes a defect is increased as well. In addition, the blocking membrane is sutured with the disk-shaped structure of the occluder through two circles of crossing points, and two circles of sutured points may effectively fix the blocking membrane. The occluder is pulled into a bundle when put into the sheath tube, and the suture between the two circles of sutured points may pull the two circles of sutured points, thereby reducing the possibility of the displacement of the crossing points, sutured with the suture, of the occluder. And then the possibility of the enlargement of the disk surface caused by deformation of the disk-shaped structure of the occluder is effectively reduced, and the stability of the occluder is improved. The occluder is not limited to a macromolecular material occluder, and also may be made of other materials (such as a metal material having rebound resilience lower than that of a nickel-titanium alloy wire), as long as the rebound resilience of the occluder is lower than that of an occluder made of the nickel-titanium alloy wire. The occluder is not limited to a single-layer structure, and also may be of a multilayer mesh disk structure. The blocking membrane is not limited to having two circles of sutured points, and also having three, four or more circles of sutured points depending on the clinical requirements. The occluder of the present disclosure is described below by taking a macromolecular material occluder as an example.

Figure 2:
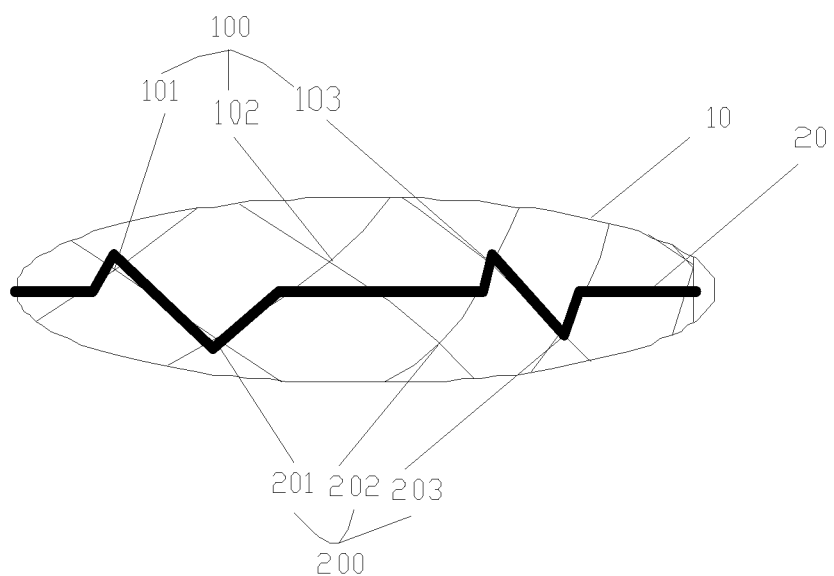
FIG. 2 is a schematic diagram of partial suturing of the occluder in FIG. 1.

Referring to FIG. 1 and FIG. 2, an occluder 1 provided by the present embodiment includes a first disk-shaped structure 10 having grids and a blocking membrane 20 arranged on the first disk-shaped structure 10.

The first disk-shaped structure 10 may be woven by at least two groups of weaving wires in an intertwined manner. The first disk-shaped structure 10 having grids may be woven by a macromolecular material which may be one or several of PET (Polyethylene Terephthalate), PLA (Poly-L-lactide Acid), PGA (Poly-glycolide), PHA (Poly-hydroxyalkanoate), PDO (Poly-dioxanone) and PCL (Poly-caprolactone). In the present embodiment, the first disk-shaped structure 10 is woven by two groups of weaving wires in the intertwined manner.

In the first disk-shaped structure 10, the two groups of weaving wires are crossed to form multiple circles of crossing points. Each circle of crossing points includes multiple crossing points. The multiple crossing points at the same circle of crossing points are uniformly distributed along a circumferential direction of this circle (namely the distance between two adjacent crossing points along the circumferential direction of this circle is equal). Each crossing point is formed by crossing two groups of weaving wires having different turning directions. The multiple circles of crossing points include an outermost circle of crossing points 100 of the occluder 1 and a first circle of crossing points 200 closest to the outermost circle of crossing points 100. The multiple circles of crossing points further include a second circle of crossing points, a third circle of crossing points and the like. The second circle of crossing points are located in the inner side of the first circle of crossing points, and the third circle of crossing points are located in the inner side of the second circle of crossing points, and the rest can be arranged in the same manner.

Figure 3:
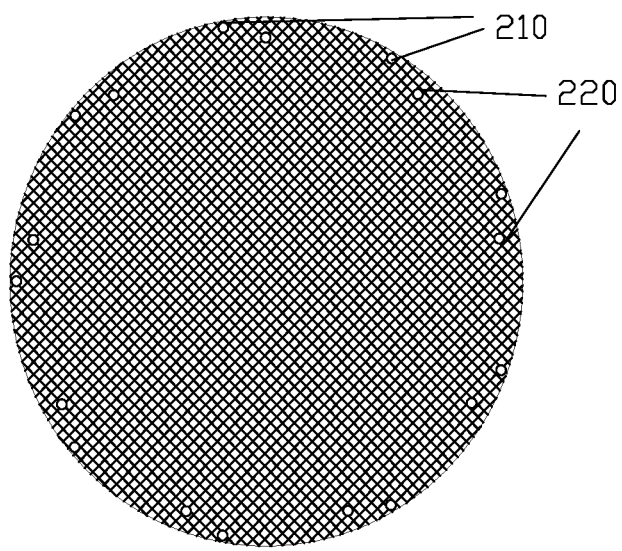
FIG. 3 is a structural schematic diagram of a blocking membrane of the occluder in FIG. 2.

Referring also to FIG. 3, the shape and the size of the blocking membrane 20 are determined according to the shape and the size of the first disk-shaped structure 10. In the present embodiment, the blocking membrane 20 is round and has a diameter equal to the maximum diameter of the first disk-shaped structure 10, so as to ensure that the blocking membrane 20 may be put into the first disk-shaped structure 10 and also abut against the edge of the first disk-shaped structure 10, and then to allow the blocking membrane 20 to completely cover the largest section of the first disk-shaped structure 10.

In the present embodiment, the edge of the blocking membrane 20 is provided with a first circle of sutural pores 210 and a second circle of sutural pores 220. Each circle of sutural pores includes multiple sutural pores. The first circle of sutural pores 210 is formed in the edge position of the blocking membrane 20, and the distance between every two adjacent sutural pores in the first circle of sutural pores 210 along the circumferential direction of this circle is equal (namely the multiple sutural pores in the first circle of sutural pores 210 are uniformly distributed in the circumferential direction of this circle). The second circle of sutural pores 220 is formed in the inner side of the first circle of sutural pores 210, and the distance between every two adjacent sutural pores in the second circle of sutural pores 220 along the circumferential direction of this circle is equal (namely the multiple sutural pores in the second circle of sutural pores 220 are uniformly distributed in the circumferential direction of this circle). One sutural pore in one second circle of sutural pores 220 is located between every two adjacent sutural pores in the first circle of sutural pores 210.

It can be understood that in other embodiments, the distance between every two adjacent sutural pores in the first circle of sutural pores 210 along the circumferential direction of this circle also may be not equal (namely the multiple sutural pores in the first circle of sutural pores 210 are non-uniformly distributed in the circumferential direction of this circle). And the distance between every two adjacent sutural pores in the second circle of sutural pores 220 along the circumferential direction of this circle also may be not equal (namely the multiple sutural pores in the second circle of sutural pores 220 are non-uniformly distributed in the circumferential direction of this circle). As long as there is at least one sutural pore of the second circle of sutural pores 220 positioned between two adjacent sutural pores of the first circle of sutural pores 210.

Preferably, the number of the sutural pores in the first circle of sutural pores 210 is less than the number of the crossing points in the outermost circle of crossing points 100. In the present embodiment, the number of the sutural pores in the first circle of sutural pores 210 is half of the number of the crossing points in the outermost circle of crossing points 100. When the blocking membrane 20 is sutured to the first disk-shaped structure 10, two adjacent sutural pores in the first circle of sutural pores 210 directly skip over one crossing point in the outermost circle of crossing points 100, so that after the blocking membrane 20 is sutured, half of the crossing points in the outermost circle of crossing points 100 are sutured at the edge of the blocking membrane 20 through a suture passing through the sutural pores in the first circle of sutural pores 210, and the number of the sutured points on the circumference of the maximum diameter of the first disk-shaped structure 10 is decreased, thereby reducing the radial length of the first disk-shaped structure 10 after being bound into a bundle.

The edge of the blocking membrane 20 is sutured to the outermost circle of crossing points 100 through a suture 70 passing through the first circle of sutural pores 210. The position close to the edge of the blocking membrane 20 is sutured to one circle of crossing points, located within the outermost circle of crossing points 100, through a suture passing through the second circle of sutural pores 220. Therefore, when placed into the sheath tube, the occluder 1 is axially stretched into a bundle, and the blocking membrane 20 deforms with it. As the sutural pores of the blocking membrane 20 are respectively sutured to the outermost circle of crossing points 100 and one circle of crossing points located within the outermost circle of crossing points 100, when the occluder 1 is axially stretched into the bundle, sutured points of the blocking membrane 20 are located on different sections. When the occluder 1 is placed into the sheath tube, the section where the outermost circle of crossing points 100 is located is the largest section of the occluder 1. Partial sutured points are located on other circles of crossing points, so that after the occluder 1 deforms into the bundle, the area of the largest section of the occluder 1 is reduced along with the decrease in the number of the sutured points, so that it would be easier to place the occluder 1 into the sheath tube. Furthermore, the area of the largest section of the occluder 1 is reduced, so that the friction and squeezing of the opening of the sheath on the occluder 1 are correspondingly reduced. Meanwhile, the number of pushing points of the opening of the sheath tube to the edge of the blocking membrane 20 is decreased due to the decrease in the number of the sutured points of the largest section, so that the deformation of the disk-shaped structure of the occluder 1 due to the squeezing on the sutured points is reduced. In addition, after the blocking membrane 20 is sutured to the outermost circle of crossing points 100 and the circle of crossing points located within the outermost circle of crossing points 100 of the first disk-shaped structure 10, as one sutural pore in one second circle of sutural pores 220 is located between every two adjacent sutural pores in the first circle of sutural pores 210, after the occluder has been released from the sheath tube, the circle of crossing points located within the outermost circle of crossing points 100 and sutured with the blocking membrane 20 would move towards the blocking membrane 100. This circle of crossing points will also push the movement of the edge of the blocking membrane between two adjacent crossing points sutured with the blocking membrane 20 in the outermost circle of crossing points 100 more effectively, and then the blocking membrane may be more gently contained within the first disk-shaped structure 10, which reduces the possibility that the edge of the blocking membrane 20 will roll up in the natural state, and thereby improve the safety and effectiveness of occlusion.

Further, to achieve a better occlusion effect, in the present embodiment, the second circle of sutural pores are sutured to the first circle of crossing points 200 of the occluder, and the first circle of crossing points 200 are the circle of crossing points closest to the outermost circle of crossing points 100.

After being sutured, slight deformation occurs when the blocking membrane 20 is pulled due to the elasticity of the blocking membrane 20 itself. However, the second circle of sutural pores 220 are relatively close to the first circle of sutural pores 210, which can effectively prevent plastic deformation of the blocking membrane and reduce the risk of damage to the blocking membrane 20 under the action of a pulling force.

It can be understood that in the natural state (in which the occluder 1 is unbundled), the second circle of crossing points 200 here may be closer to the distal end of the occluder 1 than the outermost circle of crossing points 100, and also may be closer to the proximal end of the occluder 1 than the outermost circle of crossing points 100.

It can be understood that in other embodiments, the first circle of sutural pores 210 and/or the second circle of sutural pores 220 may be omitted, as long as the edge of the blocking membrane 20 and a position close to the edge of the blocking membrane 20 may be sutured to the outermost circle of crossing points 100 and the first circle of crossing points 200, respectively, through the sutures. And the number of the crossing points sutured with the blocking membrane 20 in the outermost circle of crossing points 100 is less than that of all the crossing points in the outermost circle of crossing points 100.

In the present embodiment, the blocking membrane 20 is sutured to the crossing points of the first disk-shaped structure 10 through a suture 70. The suture 70 is a polylactic acid suture 70, and the blocking membrane 20 is a polylactic acid blocking membrane. The polylactic acid is a degradable material, which may be absorbed by a human body. It can be understood that the materials of the suture and the blocking membrane also may be other materials capable of being absorbed by the human body and harmless to the human body, and there is no specific limitation.

Figure 4:
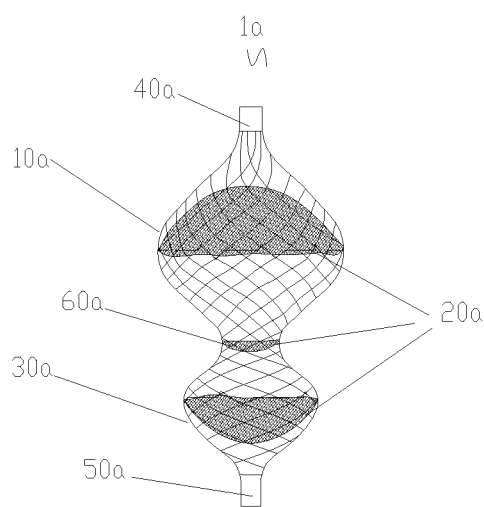
FIG. 4 is a structural schematic diagram of an occluder provided by another embodiment of the present disclosure.

Referring to FIG. 4, in another embodiment of the present disclosure, the occluder 1a further includes a second disk-shaped structure 30a and a waist part 60a connecting the first disk-shaped structure 10a with the second disk-shaped structure 30a. The second disk-shaped structure 30a has the same structure as the first disk-shaped structure 10a. Further, the first disk-shaped structure 10a and the second disk-shaped structure 30a communicate through the waist part 60a to form an "I" shape. When occluding a heart defect, the first disk-shaped structure 10a and the second disk-shaped structure 30a are respectively used for abutting against two side walls of a defective atrial septum, so as to occlude the heart defect. It can be understood that the occluder also may be of any other shape. The structure of the occluder in the present embodiment is merely exemplary, but not intended to limit the structure of the present disclosure. Those of ordinary skill in the art can select any proper structures under the enlightenment of the present disclosure.

In the present embodiment, the occluder 1a is woven by two groups of weaving wires. The distal end of the first disk-shaped structure 10a is provided with a distal sealing head 40a, and first ends of the two groups of weaving wires are collected at the distal sealing head 40a. The proximal end of the second disk-shaped structure 30a is provided with a proximal sealing head 50a, and second ends of the two groups of weaving wires are collected at the proximal sealing head 50a. The structures and the shapes of the proximal sealing head 50a and the distal sealing head 40a are not specifically limited. In the present embodiment, the proximal sealing head 50a and the distal sealing head 40a are both designed into cylindrical structures.

In FIG. 4, 20a are blocking membranes.

In a conventional occluder, the number of the weaving wires is generally an even number, specifically 36, 72, 144 and the like, and there is no specific limitation to this. In the present embodiment, the occluder 1a is woven by 36 weaving wires; therefore, the number of crossing points in the outermost circle of the crossing points formed is 18, and there are 9 sutured points between the blocking membrane and the outermost circle of crossing points, and 9 sutured points between the blocking membrane and the first circle of crossing points, which greatly reduce the area of the section of the occluder 1a that is being placed into the sheath tube.

A suturing method of a blocking membrane of an occluder according to one embodiment of the present disclosure is described below in combination with the accompanying drawing.

Referring to FIG. 2 and FIG. 3 together, first, the number and positions of sutured points on a blocking membrane 20 are determined according to the number of crossing points in the outermost ring of crossing points on the occluder 1, and a cut circular polylactic acid blocking membrane 20 is placed into a first disk-shaped structure 10 through a grid of the pre-shaped occluder 1 by using a pair of forceps. Second, the blocking membrane 20 is flattened by the forceps and evenly placed in the first disk-shaped structure 10 to ensure that the edge of the blocking membrane 20 is fitted to the edge of the disk surface of the first disk-shaped structure 10. Third, the outermost circle of crossing point 100 adjacent to the edge of the disk surface and a first circle of crossing point 200 are selected, and the edge of the blocking membrane 20 is placed between the selected upper and lower circles of crossing points. A needle threaded with a polylactic acid suture is threaded through a first circle of sutural pores 210 at the edge of the blocking membrane 20 and routed to one crossing point 101 in the outermost circle of crossing points to hook the crossing point from the inner upper side to the outer lower side of this crossing point, and then moves to one crossing point 201 of the adjacent first circle of crossing point 200. The needle threaded with the polylactic acid suture is threaded through a second circle of sutural pores 220 at the edge of the blocking membrane 20 to hook the crossing point 201 from the outer lower side to the inner upper side, and then bypasses two weaving wires, namely skips over one crossing point 102 of the outermost circle of crossing points 100 and one crossing point 202 of the first circle of crossing points 200, and moves to one crossing point 103 of the outermost circle of crossing points 100 to hook the crossing point 103 from the inner upper side to the outer lower side, and then moves to one crossing point 203 of the first circle of crossing points 200 to hook this crossing point from the outer lower side to the inner upper side of this crossing point. In this manner, the suture is threaded anticlockwise by one circle; after 9 crossing points in the outermost circle of crossing points and 9 crossing points in the first circle of crossing points are respectively hooked, two ends of the suture are knotted three times, or the number of times of knotting may also be determined according to the actual size of the occluder as long as the knots are not loosened, so there is no specific limitation as to this feature; and the suturing of the blocking membrane 20 on the occluder is completed.

It should be noted that the suturing method provided in the present embodiment is only one of multiple implementation methods. For example, in other embodiments, the blocking membrane also may be sutured with the first circle of crossing points at first, and then is sutured with the first circle of crossing points, adjacent to the sutured points, in the outermost circle of crossing points, and the moving direction of the needle may be clockwise or anticlockwise. For the suturing method in the above embodiment, in the suturing process, the number of sutured points on a single section is decreased, but the total number of sutured points between the blocking membrane and the occluder is increased; and furthermore, two groups of sutured points may be jointly fixed, so the suturing strength between the blocking membrane and the occluder is improved. Further, it can be ensured that the number of the sutured points, working with the sheath tube, on the section is decreased when the occluder is placed into the sheath tube, so the possibility of movement of the blocking membrane under the squeezing and friction of the opening of the sheath tube is reduced, and the suturing strength between the blocking membrane and the occluder is also improved.

In the above-mentioned embodiment, when the blocking membrane 20 is sutured on the occluder 1, one crossing point in the outermost circle of crossing points and one crossing point in the first circle of crossing points are bypassed between two adjacent sutured points. In other embodiments, the number of the crossing points in the outermost circle of crossing points and the number of the crossing points in the first circle of crossing points which are bypassed between two adjacent sutured points may also be determined according to the size of the occluder and the number of weaving wires, as long as the suturing strength between the blocking membrane and the disk-shaped structure of the occluder may be guaranteed.

All technical features of the above-mentioned embodiments may be randomly combined. To simplify the description, not all possible combinations of the respective technical features in the above-mentioned embodiments are described. However, the combinations of these technical features shall all fall within the scope recorded in the description as long as they are not contradictory.

The above-mentioned embodiments only express several implementation modes of the present disclosure, and their descriptions are relatively specific and detailed, but may not be understood as limitations to the scope of the invention patent. It should be noted that those of ordinary skill in the art can further make a plurality of deformations and improvements without departing from the concept of the present disclosure, and these deformations and improvements all fall within the protection scope of the present disclosure. Therefore, the protection scope of the patent of the present disclosure shall be based on attached claims.

The invention claimed is:

1. An occluder, comprising:
a first disk-shaped structure having grids, wherein the first disk-shaped structure is woven by at least two groups of weaving wires, with the at least two groups of weaving wires crossed to form multiple circles of crossing points that include a first outermost circle of crossing points and second circle of crossing points that is adjacent to the first outermost circle of crossing points;
a blocking membrane that is arranged in the first disk-shaped structure and having a plurality of sutured points; and
wherein a suture is threaded over some of the crossing points in each of the first outermost circle of crossing points and second circles of crossing points, so that the total number of sutured points between the blocking membrane and the first outermost circle of crossing points is equal to the total number of sutured points between the blocking membrane and the second circle of crossing points.

2. The occluder according to claim 1, wherein each sutured point defines a sutural pore, and a first circle of sutural pores and a second circle of sutural pores are defined in the blocking membrane; and the first circle of sutural pores are farther from a center of the blocking membrane than the second circle of sutural pores, and the number of the sutural pores in the first circle of sutural pores is less than that of all the crossing points in the first outermost circle of crossing points.

3. The occluder according to claim 2, wherein the second circle of sutural pores are sutured to the circle of crossing points closest to the first outermost circle of crossing points in the multiple circles of crossing points through the suture.

4. The occluder according to claim 2, wherein the first circle of sutural pores are arranged at an edge of the blocking membrane.

5. The occluder according to claim 2, wherein at least one sutural pore among one second circle of sutural pores is located between every two sutural pores in the first circle of sutural pores.

6. The occluder according to claim 1, wherein the occluder further comprises a second disk-shaped structure connected with the first disk-shaped structure and a waist part connected between the first disk-shaped structure and the second disk-shaped structure.

7. The occluder according to claim 6, wherein a distal end of the first disk-shaped structure is provided with a distal sealing head, and first ends of the at least two groups of weaving wires are gathered at the distal sealing head; and a proximal end of the second disk-shaped structure is provided with a proximal sealing head, and second ends, opposite to the first ends, of the at least two groups of weaving wires are gathered at the proximal sealing head.

* * * * *